(12) United States Patent
Sakai et al.

(10) Patent No.: US 9,267,900 B2
(45) Date of Patent: Feb. 23, 2016

(54) METHOD FOR MEASURING THREAD ELEMENT AT END PORTION OF PIPE OR TUBE

(75) Inventors: Kenta Sakai, Tokyo (JP); Tatsuro Honda, Tokyo (JP); Seiji Hiraoka, Tokyo (JP)

(73) Assignee: NIPPON STEEL & SUMITOMO METAL CORPORATION, Tokyo (JP)

( * ) Notice: Subject to any disclaimer, the term of this patent is extended or adjusted under 35 U.S.C. 154(b) by 0 days.

(21) Appl. No.: 14/343,903

(22) PCT Filed: Sep. 13, 2011

(86) PCT No.: PCT/JP2011/070785
§ 371 (c)(1),
(2), (4) Date: Mar. 10, 2014

(87) PCT Pub. No.: WO2013/038485
PCT Pub. Date: Mar. 21, 2013

(65) Prior Publication Data
US 2014/0226154 A1    Aug. 14, 2014

(51) Int. Cl.
*G01N 21/00* (2006.01)
*G01N 21/95* (2006.01)
(Continued)

(52) U.S. Cl.
CPC ............ *G01N 21/9515* (2013.01); *B08B 1/002* (2013.01); *B08B 1/04* (2013.01); *B08B 3/022* (2013.01); *B08B 9/021* (2013.01); *B08B 9/023* (2013.01); *G01B 11/2425* (2013.01)

(58) Field of Classification Search
CPC .... B08B 9/021; B08B 9/023; G01B 11/2425; G01B 11/24; G01B 5/204; G01B 5/163; G01N 21/88; G01N 21/952; G01N 2291/2691

USPC .......... 356/237.1–237.5, 625, 630–631, 635; 348/86
See application file for complete search history.

(56) References Cited

U.S. PATENT DOCUMENTS 4,598,998 A  *  7/1986  Kamei et al. ................ 356/237.5
4,704,986 A  *  11/1987  Remp ................... B08B 9/0433
                                                    118/317

(Continued)

FOREIGN PATENT DOCUMENTS

CN          1358580        7/2002
JP          61-15749       1/1986

(Continued)

OTHER PUBLICATIONS

Masao Ogasawara, "Current Status ... for OCTG (in Japanese)", Iron and Steel : Journal of Iron and Steel institute of Japan, vol. 79, No. 5, pp. N352-N355, May 1, 1993.

*Primary Examiner* — Hoa Pham
(74) *Attorney, Agent, or Firm* — Clark & Brody

(57) ABSTRACT

The present invention provides a method for automatically measuring a thread element at an end portion of a pipe or tube P after thread processing, on a thread processing line 100 in which thread processing is performed on the end portion of each pipe or tube P which is successively conveyed, comprising: a cleaning step of cleaning the end portion of the pipe or tube by a thread cleaning apparatus 30 after the thread processing; a drying step of drying the end portion of the pipe or tube P cleaned in the cleaning step by a thread drying apparatus 40; and a measuring step of measuring the thread element at the end portion of the pipe or tube P by an automatic thread element measurement 50 after drying, wherein the end portion of the pipe or tube is put under a clean atmosphere at least in the measuring step.

5 Claims, 7 Drawing Sheets

(51) Int. Cl.
*G01B 11/24* (2006.01)
*B08B 1/00* (2006.01)
*B08B 1/04* (2006.01)
*B08B 3/02* (2006.01)
*B08B 9/02* (2006.01)
*B08B 9/023* (2006.01)

(56) References Cited

U.S. PATENT DOCUMENTS 5,521,707 A * 5/1996 Castore et al. ............... 356/394
6,027,568 A * 2/2000 Wallace et al. ............... 118/668
6,111,601 A   8/2000 Adachi

FOREIGN PATENT DOCUMENTS

| | | |
|---|---|---|
| JP | 1-124282 | 8/1989 |
| JP | 3-57606 | 6/1991 |
| JP | 6-11881 | 2/1994 |
| JP | 63-212808 | 9/1998 |
| JP | 3552440 | 5/2004 |
| JP | 2011-203220 | 10/2011 |
| WO | 97/47394 | 12/1997 |
| WO | 02/16081 | 2/2002 |

* cited by examiner

Figure 4A
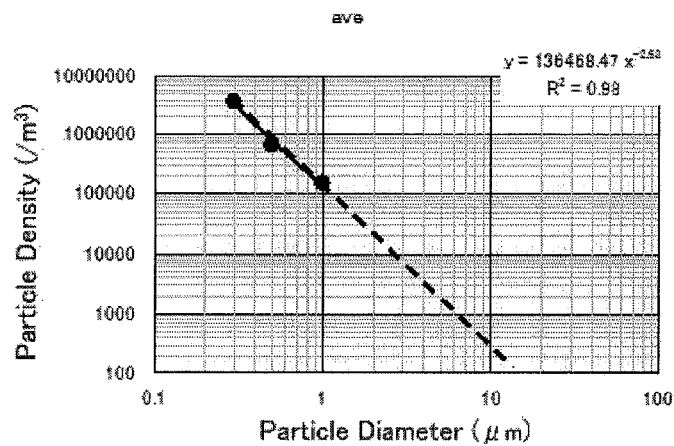
Figure 4B
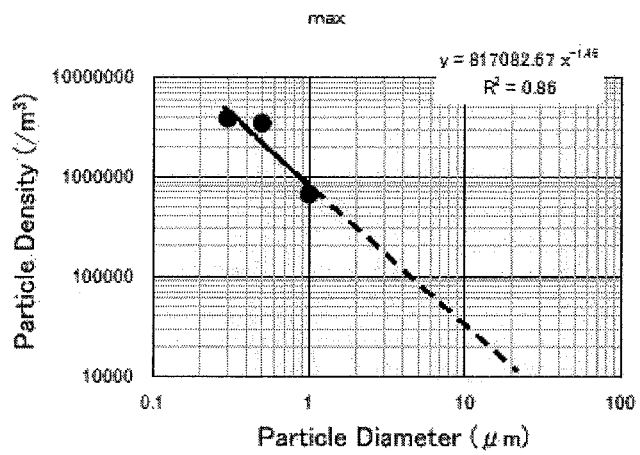
Figure 4C
| Particle Diameter (μm) | Evaluation Criterion | Number of Particles | |
|---|---|---|---|
| | | φ178mm | φ60mm |
| 1 | Average | 0.1467 | 0.1593 |
| | Maximum | 0.6703 | 0.7278 |
| 5 | Average | 0.0019 | 0.0021 |
| | Maximum | 0.0760 | 0.0826 |
| 10 | Average | 0.0003 | 0.0003 |
| | Maximum | 0.0276 | 0.0300 |

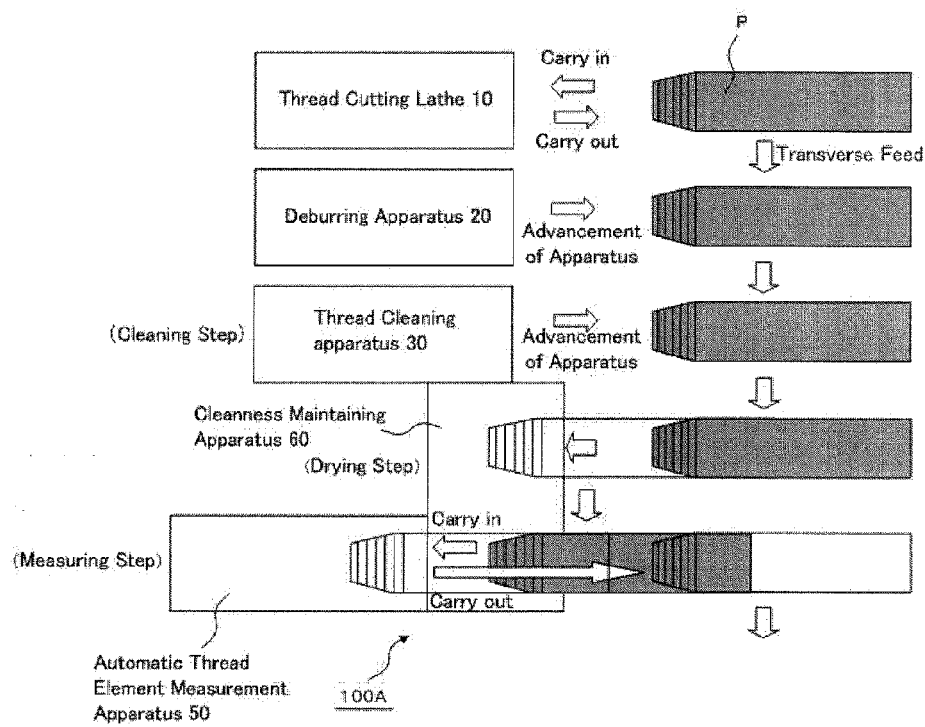

Figure 6A
Figure 6B
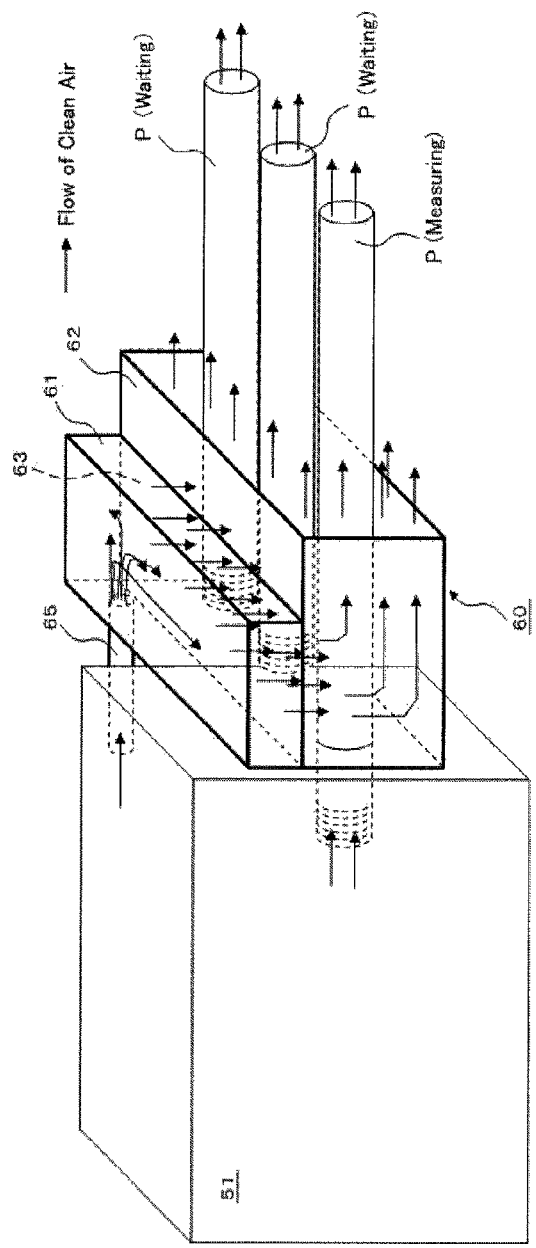
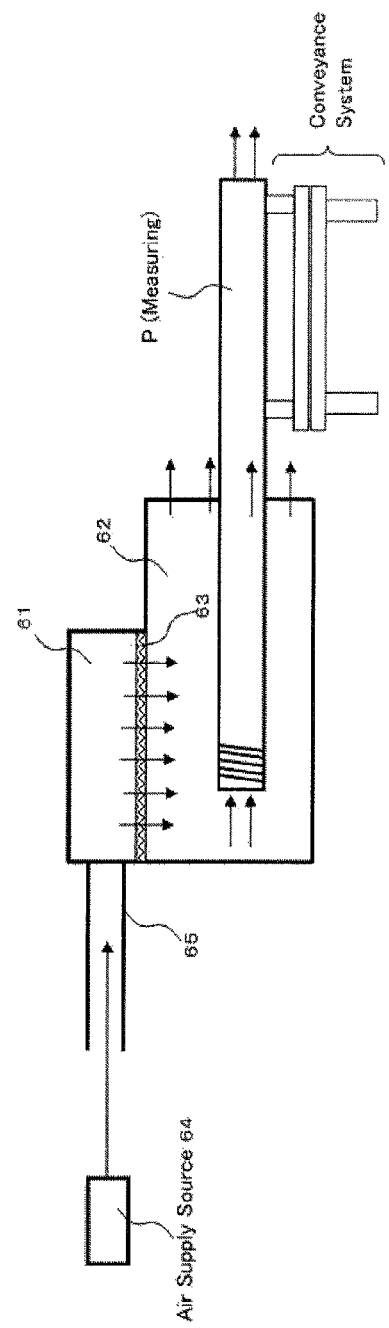

METHOD FOR MEASURING THREAD ELEMENT AT END PORTION OF PIPE OR TUBE

TECHNICAL FIELD

The present invention relates to a method for precisely measuring, automatically and on-line, thread elements at an end portion of a pipe or tube formed with a thread such as OCTG (Oil Country Tubular Goods). Hereinafter, "pipe or tube" is referred to as "pipe" when deemed appropriate.

BACKGROUND ART

Traditionally, OCTG and the like have been used by connecting end portions of pipes thereof with threads formed at those end portions of pipes. Such threads have been subjected to various improvements such as in the thread shape in association with demands for deepening of oil wells, and higher resistance to corrosive environments (see, for example, Non Patent Literature 1). Such threads, which may possibly be formed at an end portion of a pipe having a length of several tens of meters and a weight of as large as several hundreds of kgf, have a complex and high precision thread shape. Meanwhile, regarding such threads, quality control items called thread elements are defined, and whether or not a measured value of a thread element is within a predetermined tolerance is inspected. Examples of the thread element include an outer diameter of the thread part, an outer diameter of the sealing part, an outer diameter of the parallel part, a diameter of the thread groove, a height of the thread ridge, a depth of the thread groove, a thread taper, a seal taper, and the like.

While, conventionally, thread elements, which are the quality control items as described above, have been manually measured on-line (on a thread processing line) by use of a special purpose measurement instrument, attempts have been made to develop more precise automatic measurement technique in the view point of labor saving, suppression of human errors, and enhancement of the speed and precision of measurement.

Specifically, as a technique for automatically measuring thread elements, there is known an automatic measurement apparatus which has an optical sensor, which projects parallel light from a light source onto thread grooves and detects the light that leaks out to the opposite side of the light source with respect to the pipe axis, and measures thread elements based on the detection result of the optical sensor (see, for example, Patent Literatures 1 and 2).

CITATION LIST

Non Patent Literature

[Non Patent Literature 1] Masao Ogasawara, "Current Status of Tubular Connectors for OCTG (in Japanese)," Iron and Steel: Journal of Iron and Steel Institute of Japan, Vol. 79, No. 5, PP. N352-N355, May 1, 1993.

Patent Literature

[Patent Literature 1] JP3552440B
[Patent Literature 2] JP63-212808A

SUMMARY OF INVENTION

Technical Problem

However, there are environmental problems in applying on-line (on a thread processing line) an automatic measurement apparatus of thread elements as described in Patent Literatures 1 and 2.

To be Specific, when an end portion of a pipe is subjected to thread processing, generally, the end portion of the pipe is subjected to thread cutting by use of a lathe while a lubricant (water and a rust preventive agent) is sprayed onto the end portion of the pipe so that the lubricant may remain on the end portion of the pipe after thread cutting, causing deterioration of the measurement precision of thread elements. Further, when deburring is performed after cutting, in addition to any lubricant which remains as with during thread cutting, cutting chips which adhere to the end portion of the pipe as a result of deburring may cause deterioration of the measurement precision of thread elements.

For this reason, it is practically difficult to apply an automatic measurement apparatus of thread elements on-line to perform 100 percent measurement. Therefore, conventionally, pipes are picked up at appropriate timings from the thread processing line, and automatic measurement is performed after any lubricant and cutting chips are removed in a laboratory under a good environmental condition.

The present invention has been made to solve the above described technical problems, and has its object to provide a method for precisely measuring, automatically and on-line (on a thread processing line), thread elements at an end portion of a pipe formed with a thread.

Solution to Problem

In order to solve the above-described problems, the present invention provides a method for automatically measuring a thread element at an end portion of a pipe or tube after thread processing is performed on the end portion of the pipe or tube, on a thread processing line in which thread processing is performed on the end portion of each pipe or tube which is successively conveyed, comprising: a cleaning step of cleaning the end portion of the pipe or tube after the thread processing is performed on the end portion of the pipe or tube; a drying step of drying the end portion of the pipe or tube after the end portion of the pipe or tube is cleaned in the cleaning step; and a measuring step of measuring the thread element at the end portion of the pipe or tube after the end portion of the pipe or tube is dried in the drying step, wherein the end portion of the pipe or tube is put under a clean atmosphere at least in the measuring step.

Since the present invention includes a cleaning step of cleaning the end portion of the pipe or tube after thread processing is performed on the end portion of the pipe or tube, it can be expected that any lubricant remaining on the end portion of the pipe or tube during thread cutting and deburring, and cutting chips having adhered to the end portion of the pipe or tube as a result of deburring, which may cause deterioration of the measurement precision of thread elements, are cleaned. For the cleaning of an end portion of a pipe or tube in the cleaning step, for example, an organic solvent is used.

Moreover, since the present invention includes a drying step of drying the end portion of the pipe or tube after the end portion of the pipe or tube is cleaned in the cleaning step, the organic solvent, which may remain on the end portion of the pipe or tube in the cleaning step, dries, making it possible to prevent the deterioration of measurement precision of thread elements caused by the organic solvent and the like.

Further, since the present invention includes a measuring step of measuring the thread element at the end portion of the pipe or tube which is put under a clean atmosphere, it is possible to precisely measure the thread element. For the measurement of thread elements in the measuring step, for example, an automatic optical measurement apparatus as described in Patent Literatures 1 and 2 is used.

As so far described, according to the present invention, it is possible to precisely measure, automatically and on-line (on a thread processing line), the thread element at an end portion of a pipe formed with a thread.

Preferably, in the present invention, the end portion of the pipe or tube is put under a clean atmosphere at least during a period from the drying step to the measuring step after thread processing is performed on the end portion of the pipe or tube.

If an end portion of a pipe or tube is exposed to the atmosphere of the thread processing line after any lubricant remaining on the end portion of the pipe or tube and cutting chips having adhered to the end portion of the pipe or tube are cleaned in the cleaning step, and the end portion of the pipe or tube is dried in the drying step, there is a risk that particles existing in the atmosphere in the thread processing line adhere to the end portion of the pipe or tube, causing deterioration of measurement precision of thread elements.

However, according to the above described preferable method, since the end portion of the pipe or tube is put under a clean atmosphere at least during a period from the drying step to the measuring step, a risk that particles existing in the atmosphere of the thread processing line adhere to the end portion of the pipe or tube, thereby deteriorating the measurement precision of thread elements is reduced, thereby making it possible to measure thread elements with even more precision.

In order to solve the above-described problems, the present invention also provides a method for automatically measuring a thread element at an end portion of a pipe or tube after thread processing is performed on the end portion of the pipe or tube, on a thread processing line in which thread processing is performed on the end portion of each pipe or tube which is successively conveyed, comprising: a cleaning step of cleaning the end portion of the pipe or tube by ejecting granular dry ice with compressed air onto the end portion of the pipe or tube after thread processing is performed on the end portion of the pipe or tube; and a measuring step of measuring the thread element at the end portion of the pipe or tube after the end portion of the pipe or tube is cleaned in the cleaning step, wherein the end portion of the pipe or tube is put under a clean atmosphere at least in the measuring step.

Since the present invention also includes a cleaning step of cleaning the end portion of the pipe or tube after thread processing is performed on the end portion of the pipe or tube, it can be expected that any lubricant remaining on the end portion of the pipe or tube during thread cutting and deburring, and cutting chips having adhered to the end portion of the pipe or tube as a result of deburring, which may cause deterioration of measurement precision of thread elements, are cleaned.

Moreover, since in the cleaning step of the present invention, the end portion of the pipe or tube is cleaned by ejecting granular dry ice with compressed air after thread processing is performed on the end portion of the pipe or tube, the dry ice used for cleaning will spontaneously evaporate. For this reason, there is an advantage that the drying step of drying the cleaned end portion of the pipe or tube is obviated.

Further, since the present invention includes a measuring step of measuring the thread element at the end portion of the pipe or tube which is put under a clean atmosphere, it is possible to precisely measure the thread element. For the measurement of the thread element in the measuring step, for example, an automatic optical measurement apparatus as described in Patent Literatures 1 and 2 is used.

As so far described, according to the present invention, it is possible to precisely measure automatically and on-line (on a thread processing line) thread elements at an end portion of a pipe formed with a thread.

Advantageous Effects of Invention

According to the method for measuring a thread element at an end portion of a pipe or tube relating to the present invention, it is possible to precisely measure, automatically and on-line (on a thread processing line), thread elements at an end portion of a pipe or tube formed with a thread. As a result of that, it is expected to enable 100 percent measurement on-line.

BRIEF DESCRIPTION OF DRAWINGS

FIGS. 4A, 4B, and 4C are diagrams to show results of a test to evaluate the effect of particles existing in the atmosphere of a thread processing line.

FIG. 5 is a schematic diagram to show a general configuration of a thread processing line for carrying out the method for measuring a thread element at an end portion of a pipe relating to a second embodiment of the present invention.

FIGS. 6A and 6B are schematic diagrams to show an example of the cleanness maintaining apparatus shown in FIG. 5.

DESCRIPTION OF EMBODIMENTS

Hereafter, embodiments of the present invention will be described appropriately referring to the appended drawings.

First Embodiment

Figure 1:
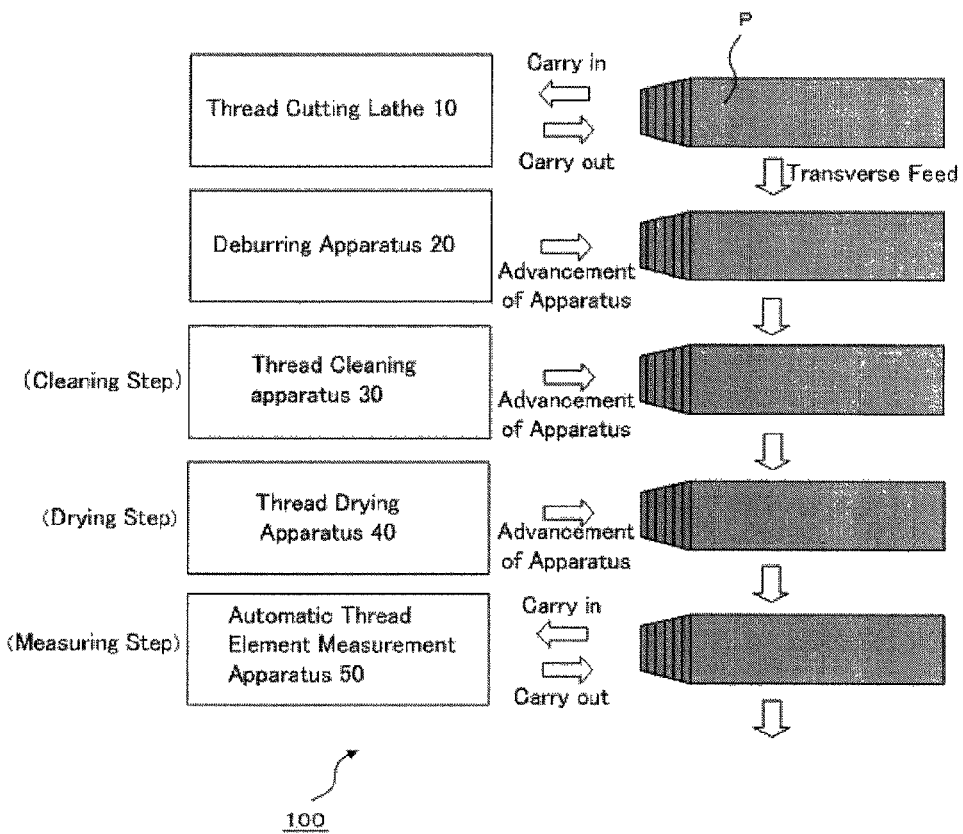
FIG. 1 is a schematic diagram to generally show a thread processing line for carrying out a method for measuring a thread element at an end portion of a pipe relating to a first embodiment of the present invention.

FIG. 1 is a schematic diagram to generally show a thread processing line for carrying out a method for measuring a thread element at an end portion of a pipe relating to a first embodiment of the present invention.

As shown in FIG. 1, thread processing is performed on an end portion of each pipe P, which is successively conveyed by a predetermined conveyance system (not shown) in a thread processing line 100.

Specifically, first, a pipe P is carried in the pipe axial direction to an installation position of a thread cutting lathe 10. Next, an end portion of the pipe P is subjected to thread cutting by the thread cutting lathe 10 while a lubricant (water and a rust prevention agent) is sprayed onto the end portion of the pipe P. The pipe P for which thread cutting on the end portion of the pipe is finished is carried out in the pipe axial direction from the thread cutting lathe 10, and is transversely fed to a position opposing the installation position of a deburring apparatus 20.

Next, the deburring apparatus 20 advances in the pipe axial direction toward the end portion of the pipe P. Then, deburring of the end portion of the pipe P is performed by the deburring apparatus 20. As the deburring apparatus 20, for example, a lathe similar to the thread cutting lathe 10 is used. That is, burrs generated on the thread of the end portion of the pipe P is removed by the deburring apparatus 20 while a lubricant (water and a rust prevention agent) is sprayed on the end portion of the pipe P. The deburring apparatus 20 retreats to its original position after finishing the deburring of the end portion of the pipe P.

As so far described, the pipe P which has been subjected to thread processing on its end portion is transversely fed to a position opposing the installation position of a thread cleaning apparatus 30, and a cleaning step of cleaning the end portion of the pipe after thread processing is performed. Specifically, the thread cleaning apparatus 30 advances in the pipe axial direction toward the end portion of the pipe P, and cleaning with an organic solvent is performed.

Figure 2A:
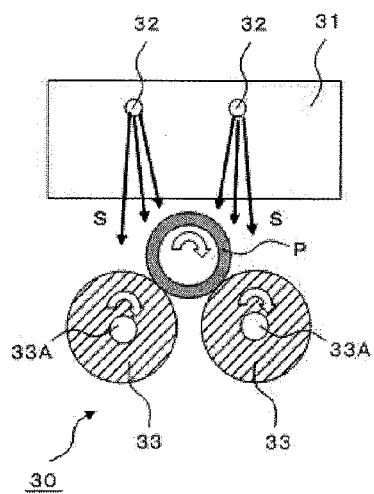
FIGS. 2A and 2B are schematic diagrams to generally show an example of the thread cleaning apparatus shown in FIG. 1.
Figure 2B:
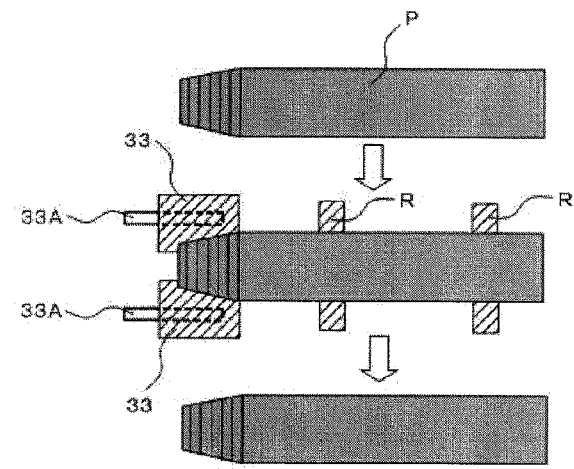

FIGS. 2A and 2B are schematic diagrams to generally show an example of the thread cleaning apparatus 30 which can be used in the cleaning step of the present embodiment. FIG. 2A shows a partial perspective front view (seeing through the interior of a housing 31), and FIG. 2B shows a plan view. It is noted that illustration of the housing 31 and a nozzle 32 is omitted in FIG. 2B.

As shown in FIGS. 2A and 2B, the thread cleaning apparatus 30 of the present embodiment includes a housing 31 positioned above the pipe P, a nozzle 32 incorporated in the housing 31, and a cleaning brush 33 positioned below the pipe P, the cleaning brush 33 being rotatable around an axis 33A. The housing 31, the nozzle 32, and the cleaning brush 33 advance as a single body in the axial direction of the pipe P toward an end portion of the pipe P until the nozzle 32 is positioned immediately above the threaded end portion of the pipe P, and the cleaning brush 33 is positioned immediately below the threaded end portion of the pipe P. Then, after the advance action is finished, an organic solvent S as a cleaning liquid is ejected from the nozzle 32. The organic solvent S ejected from the nozzle 32 is sprayed onto the end portion of the pipe P through an opening on a lower surface of the housing 31. In this occasion, the end portion of the pipe P is rubbed with the cleaning brush 33 by causing a turning roller R to circumferentially rotate the pipe P, and causing the cleaning brush 33 to rotate around the axis 33A. As a result of the above described actions, the entire circumference of the end portion of the pipe P is cleaned, and it can be expected that any lubricant remaining on the end portion of the pipe during thread cutting and deburring, and cutting chips having adhered to the end portion of the pipe as a result of deburring are removed.

The thread cleaning apparatus 30 retreats to its original position after finishing the cleaning of the end portion of the pipe P.

Next, as shown in FIG. 1, the pipe P whose end portion is cleaned is transversely fed to a position opposing the installation position of the thread drying apparatus 40, and a drying step of drying the end portion of the pipe P is performed. Specifically, the thread drying apparatus 40 advances in the pipe axial direction toward the end portion of the pipe P, and drying by air is performed.

Figure 3A:
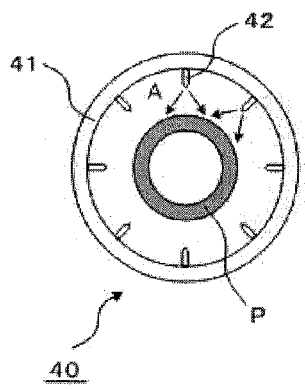
FIGS. 3A and 3B are schematic diagrams to generally show an example of the thread drying apparatus shown in FIG. 1.
Figure 3B:
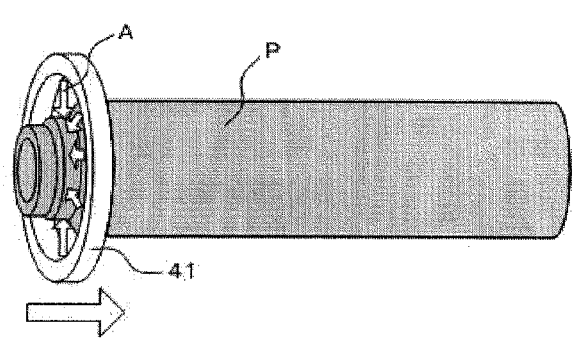

FIGS. 3A and 3B are schematic diagrams to generally show an example of the thread drying apparatus 40 which can be used in the drying step of the present embodiment. FIG. 3A shows a front view, and FIG. 3B shows a perspective view. It is noted that illustration of a nozzle 42 is omitted in FIG. 3B.

As shown in FIGS. 3A and 3B, the thread drying apparatus 40 of the present embodiment includes an annular member 41 having an inner diameter larger than the outer diameter of the pipe P, and a plurality of nozzles 42 attached to the annular member 41. The annular member 41 and the nozzles 42 advance as a single body toward the end portion of the pipe P to a position where they surround the threaded end portion of the pipe P. Then, after the advance action is finished, air A is ejected from the nozzle 42 toward the end portion of the pipe P. As a result of the above described actions, it is expected that the organic solvent S, which may remain on the end portion of the pipe P in the above described cleaning step, can be dried.

The thread drying apparatus 40 retreats to its original position after finishing the drying of the end portion of the pipe P.

Finally, as shown in FIG. 1, the pipe P whose end portion is dried is transversely fed to a position opposing the installation position of an automatic thread element measurement apparatus 50 so that a measuring step of measuring thread elements at the end portion of the pipe after drying is performed under a clean atmosphere. Specifically, the end portion of the pipe P is carried in the pipe axial direction toward the installation position of the automatic thread element measurement apparatus 50 which is placed under a clean atmosphere. More specifically, the automatic thread element measurement apparatus 50 is installed in a measuring chamber which is filled with clean air under a positive pressure condition, and the end portion of the pipe P is carried in into the measuring chamber from an opening portion provided in the measuring chamber so that thread elements are measured by the automatic thread element measurement apparatus 50. As the automatic thread element measurement apparatus 50, for example, an automatic optical measurement apparatus as described in Patent Literatures 1 and 2 can be used. The pipe P which has undergone the measurement of thread elements is carried out to the outside of the measuring chamber through the opening portion of the measuring chamber, and is thereafter transversely fed.

Since the method for measuring a thread element at an end portion of a pipe relating to the present embodiment described so far includes a cleaning step of cleaning the end portion of the pipe after thread processing (thread cutting and deburring) is performed on the end portion of the pipe, it can be expected that any lubricant remaining on the end portion of the pipe during thread cutting and deburring, and cutting chips having adhered to the end portion of the pipe as a result of deburring, which may cause deterioration of the measurement precision of thread elements, are cleaned.

Moreover, since the method for measuring a thread element at an end portion of a pipe relating to the present embodiment includes a drying step of drying the end portion of the pipe after the end portion of the pipe or tube is cleaned in the cleaning step, the organic solvent S which may remain on the end portion of the pipe in the cleaning step is dried, making it possible to prevent deterioration of the measurement precision of thread elements caused by the organic solvent S.

Further, since the method for measuring a thread element at an end portion of a pipe relating to the present embodiment includes a measuring step of measuring thread elements at an end portion of a pipe which is put under a clean atmosphere, it is possible to precisely measure thread elements.

It is noted that, in the present embodiment, description has been made on a mode in which the deburring apparatus 20, the thread cleaning apparatus 30, and the thread drying apparatus 40 advance in the pipe axial direction toward an end portion of the pipe P, and retreat to their original positions after the deburring, cleaning, and drying of the end portion of the pipe P are finished. However, the present invention will not be limited to such a mode, and it is also possible to adopt a mode in which the pipe P is carried in the pipe axial direction toward the installation position of each apparatus 20 to 40, and is carried out in the pipe axial direction from each apparatus 20 to 40 after the deburring, cleaning, and drying of the end portion of the pipe P are finished.

Second Embodiment

In the above described first embodiment, an end portion of the pipe P is to be exposed to the atmosphere of the thread processing line 100 for a period after the end portion of the pipe P is dried in the drying step by the thread drying apparatus 40 until thread elements at the end portion of the pipe P are measured in the measuring step by the automatic thread element measurement apparatus 50. For this reason, there is risk that particles existing in the atmosphere of the thread processing line 100 adhere to the end portion of the pipe P before thread elements at the end portion of the pipe P are measured, thereby deteriorating the measurement precision of thread elements.

Accordingly, the present inventors have conducted a test to evaluate the effects of particles existing in the atmosphere of the thread processing line 100.

First, the present inventors measured particle densities (the number of particles per a unit volume) at particle diameters of 0.3 µm, 0.5 µm, and 1.0 µm by using a particle counter over two days in the thread processing line 100. To measure the particle density, a commercially available particle counter was used.

FIG. 4A is a graph to show average values within an evaluation time of measured particle densities. FIG. 4B is a graph to show maximum values within the evaluation time of the measured particle densities. The present inventors estimated the particle densities at particle diameters of 5 µm and 10 µm by extrapolating measured values of particle densities at particle diameters of 0.3 µm, 0.5 µm, and 1.0 µm shown in FIGS. 4A and 4B (the dashed lines shown in FIGS. 4A and 4B indicate the extrapolation results).

Next, the present inventors calculated the volume of a region through which the thread part passes during the above described conveyance from a conveyance distance (supposed to be 5 m) of the thread part of the pipe P which is conveyed while being exposed to the atmosphere of the thread processing line 100, and the outer diameter and length of the thread part. Then, it was supposed that the particles existing in the calculated volume uniformly adhered to the entire thread part of the pipe P. Specifically, the particle density at a particle diameter of 1 µm measured as described above and the above described calculated volume were multiplied with each other to calculate the number of particles having a particle diameter of 1 µm which adhered to the entire thread part of the pipe P. Moreover, the particle densities at particle diameters of 5 µm and 10 µm estimated as described above and the above described calculated volume were multiplied with each other to calculate the number of particles having particle diameters 5 µm and 10 µm which adhered to the entire thread part of the pipe P.

Further, supposing a case in which an optical measurement apparatus including a light source and light receiving means was used as the thread element measurement apparatus, the present inventors assumed that a focal depth of the light receiving means was 0.2 mm and an image pickup field of the light receiving means was 5 mm×5 mm. Then, of the particles adhering to the entire thread part of the pipe P, the number of particles adhering to the above described evaluation area (5 mm×5 mm×0.2 mm) was calculated.

FIG. 4C is a diagram to show the number of particles adhering to the evaluation area, which was calculated as described above. In FIG. 4C, the numbers of particles adhering to the evaluation area are shown for both outer diameters of the pipe P of 178 mm and 60 mm.

As seen from FIG. 4C, the particles having a particle diameter of 5 µm will adhere to the evaluation area of the thread part of the pipe P at a probability of about 7 to 8% (in other words, the particles adhere to the evaluation area of the thread part in 7 to 8 pipes P out of 100 pipes P) when the number thereof is relatively large. Moreover, even particles having a particle diameter of 10 µm will adhere to the evaluation area of the thread part of the pipe P at a probability of about 3% when the number thereof is relatively large. Further, particles having a particle diameter of 1 µm will adhere to the evaluation area of the thread part of the pipe P at a probability of about 15% in an ordinary case, and at a probability of about 70% when the number thereof is relatively large.

Since a required measurement precision of thread elements is about 5 µm, the effects of the above described particles cannot be ignored when it is attempted to measure all the pipes P with high precision.

For that reason, at least during a period from the drying step (the step of drying a cleaned end portion of a pipe) to the measuring step (the step of measuring thread elements at an end portion of a pipe), the end portion of the pipe after thread processing is preferably put under a clean atmosphere. This point is taken into consideration in the second embodiment of the present invention.

Hereafter, regarding the second embodiment of the present invention, those points that differ from the above described first embodiment will be mainly described, and description on those points that are similar to the first embodiment will be appropriately omitted.

FIG. 5 is a schematic diagram to show a general configuration of a thread processing line for carrying out the method for measuring a thread element at an end portion of a pipe relating to a second embodiment of the present invention.

As shown in FIG. 5, in a thread processing line 100A of the present embodiment as well, an end portion of each pipe P, which is successively conveyed by a predetermined conveyance system (not shown) is subjected to thread processing (thread cutting and deburring). As with the first embodiment, a thread cutting lathe 10 is used for thread cutting, and a deburring apparatus 20 is used for deburring.

The pipe P which is threaded on an end portion is, as in the first embodiment, transversely fed to a position opposing the installation position of a thread cleaning apparatus 30, and cleaning step of cleaning the end portion of the pipe after thread processing is performed. Specifically, the thread cleaning apparatus 30 advances in the pipe axial direction toward the end portion of the pipe P, and cleaning with an organic solvent is performed. The thread cleaning apparatus 30 retreats to its original position after finishing the cleaning of the end portion of the pipe P.

Next, as shown in FIG. 5, the pipe P whose end portion is cleaned is transversely fed to a position opposing the installation position of a cleanness maintaining apparatus 60, and a drying step of drying the cleaned end portion of the pipe is performed. Specifically, first, the end portion of the pipe P is carried in into the cleanness maintaining apparatus 60. Then, the pipe P is transversely fed with the end portion of the pipe P being positioned in the cleanness maintaining apparatus 60, and during this period, the end portion of the pipe P is dried by clean air in the cleanness maintaining apparatus 60.

FIGS. 6A and 6B are schematic diagrams to show an example of the cleanness maintaining apparatus 60 which can be used in the present embodiment. FIG. 6A shows a perspective view, and FIG. 6B shows a side sectional view.

The cleanness maintaining apparatus 60 of the present embodiment is an application of the technical idea of "cleanness space forming apparatus" described in JP2003-248158A, proposed by the present applicant.

Specifically, as shown in FIGS. 6A and 6B, the cleanness maintaining apparatus 60 of the present embodiment includes a first chamber 61, a second chamber 62, and a mesh filter 63 for partitioning the first chamber 61 from the second chamber 62 (for example, the size of mesh shall be not more than 5 μm). One of the wall surfaces of the second chamber 62, through which the pipe P is carried in, is opened. Moreover, a part of the wall surface of the second chamber 62 on the side opposing the measuring chamber 51 in which the automatic thread element measurement apparatus 50 is installed (area through which the pipe P is carried in into the measuring chamber 51) is also opened to communicate with the measuring chamber 51.

Clean air under a positive pressure condition is supplied from an air supply source 64 which includes an air filter and a pressurizing apparatus, into the first chamber 61 of the cleanness maintaining apparatus 60 via a piping 65. The clean air supplied into the first chamber 61 passes through the mesh filter 63 and during that process, particles corresponding to the size of the mesh are removed so that the clean air is supplied to the second chamber 62. The clean air supplied to the second chamber 62 flows out to the outside via the opening portion of the second chamber 62.

The cleanness maintaining apparatus 60 which has the above described configuration makes it possible to put the end portion of the pipe P under a clean atmosphere, and at the same time to dry the end portion of the pipe P in the process of the pipe P being transversely fed.

Finally, the end portion of the pipe P is carried in into the measuring chamber 51 filled with clean air under a positive pressure condition, and thread elements are measured by an automatic thread element measurement apparatus 50 installed in the measuring chamber 51. The pipe P which has undergone the measurement of thread elements is carried out into the second chamber 62 via the measuring chamber 51 and the opening portions of the second chamber 62, and is further carried out to the outside of the second chamber 62 via the opening portion of the second chamber 62, thereafter being transversely fed.

According to the method for measuring a thread element at an end portion of a pipe relating to the present embodiment described so far, the end portion of the pipe P is put under a clean atmosphere during a period from the drying step to the measuring step. As a result of this, in addition to the advantages of the method relating to the first embodiment described above, the method relating to the present embodiment has an advantage that the risk that particles existing in the atmosphere of the thread processing line 100A adhere to an end portion of a pipe, thereby deteriorating the measurement precision of thread elements is reduced, making it possible to measure thread elements with higher precision.

It is noted that although, in the present embodiment, description has been made on a mode in which an end portion of a pipe is dried with clean air in the cleanness maintaining apparatus 60, the present invention will not be limited to such a mode. For example, it is also possible to adopt a mode in which the thread drying apparatus 40 which has been described in the first embodiment is installed in the cleanness maintaining apparatus 60 so that the end portion of the pipe is dried by this drying apparatus 40.

Moreover, although in the present embodiment, description has been made on a mode in which an end portion of the pipe P is put under a clean atmosphere during a period from the drying step to the measuring step, the present invention will not be limited to such a mode. For example, it is possible to adopt a mode in which a cleanness maintaining apparatus 60A as shown in FIG. 7 is used so that the end portion of the pipe P is put under a clean atmosphere during a period from the cleaning step to the measuring step.

Figure 7:
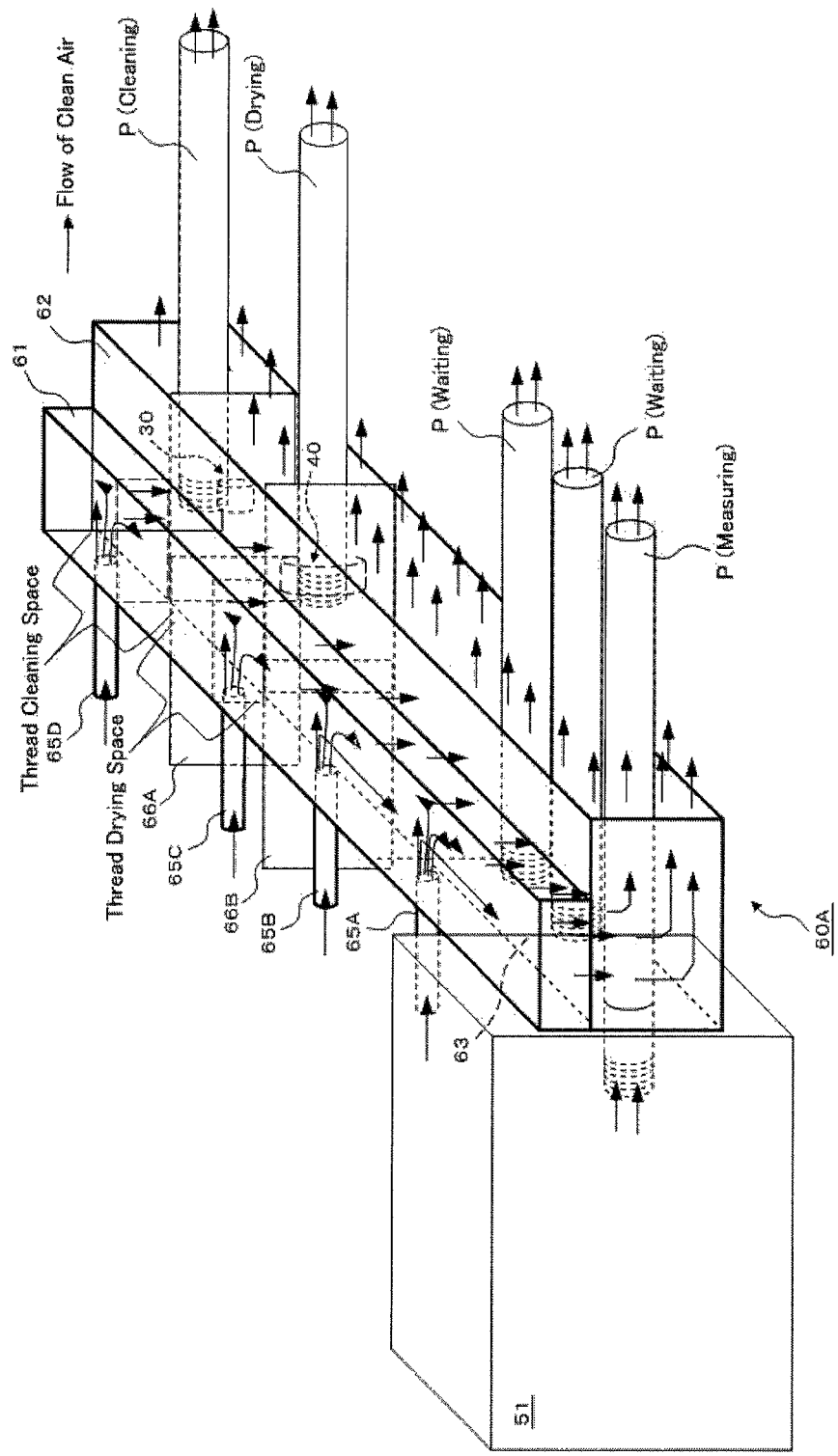
FIG. 7 is a schematic diagram to generally show a variation of the cleanness maintaining apparatus shown in FIG. 6.

Describing more specifically, in the cleanness maintaining apparatus 60A shown in FIG. 7, the thread cleaning apparatus 30 and the thread drying apparatus 40, which have been described in the first embodiment, are installed in the second chamber 62. Moreover, a space in the second chamber 62 (a thread cleaning space) in which a cleaning step is performed by using the thread cleaning apparatus 30 and a space in the second chamber 62 (a thread drying space) in which a drying step is performed by using the thread drying apparatus 40 are partitioned by a shutter 66A which is freely opened/closed. Further, the thread drying space and other spaces in the second chamber 62 are partitioned by a shutter 66B which is freely opened/closed. Clean air is supplied to the thread cleaning space via a piping 65D, clean air is supplied to the thread drying space via a piping 65C, and clean air is supplied to the other spaces in the second chamber 62 via pipings 65A and 65B.

The other configurations of the cleanness maintaining apparatus 60A are the same as those of the above described cleanness maintaining apparatus 60.

When the cleaning step is performed by the cleanness maintaining apparatus 60A having the above described configurations, an end portion of the pipe P is carried in into the thread cleaning space, and the thread cleaning apparatus 30 advances toward the end portion of the pipe P in the second chamber 62 so that cleaning with an organic solvent is performed. When this cleaning step is performed, the shutter 66A is closed to prevent an organic solvent S etc. from scattering into the adjacent thread drying space. The thread cleaning apparatus 30 retreats to its original position after finishing the cleaning of the end portion of the pipe P. Next, the shutter 66A is opened, the pipe P is transversely fed to the thread drying space with the end portion of the pipe thereof being positioned in the second chamber 62.

When the drying step is performed, the thread drying apparatus 40 advances toward an end portion of the pipe P in the second chamber 62, and drying by air is performed. When this drying step is performed, the shutter 66B is closed to prevent the organic solvent S, etc. from scattering into adjacent spaces. The thread drying apparatus 40 retreats to its original position after finishing the drying of the end portion of the pipe P. Next, the shutter 66B is opened, the pipe P is transversely fed to an adjacent space with the end portion of the pipe thereof being positioned in the second chamber 62.

Since actions hereafter are the same as those in the case where the above described cleanness maintaining apparatus 60 is used, description thereof will be omitted.

According to the method by use of the cleanness maintaining apparatus 60A described so far, since an end portion of the pipe P is put under a clean atmosphere during a period from the cleaning step to the measuring step, it can be expected to further reduce the risk that particles existing in the atmosphere in the thread processing line 100A adhere to the end portion of the pipe thereby deteriorating the measurement precision of the thread elements.

It is noted that although, in the method using the cleanness maintaining apparatus 60A described so far, description has been made on a mode in which an end portion of a pipe is dried by using the thread drying apparatus 40, it is also possible, as in the case of the cleanness maintaining apparatus 60, to adopt a mode in which the end portion of the pipe is dried by clean air in the cleanness maintaining apparatus 60A without installing the thread drying apparatus 40.

Third Embodiment

The above described first and second embodiments include a drying step of drying an end portion of a pipe P which has been cleaned. However, the present embodiment differs from the first and second embodiments in that the drying step is obviated since granular dry ice is ejected along with compressed air to clean the end portion of the pipe in the cleaning step.

Figure 8A:
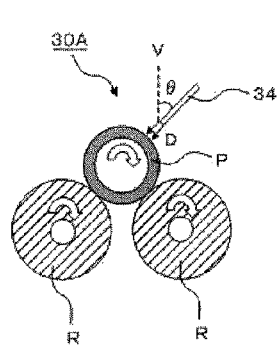
FIGS. 8A, 8B, and 8C are schematic diagrams to generally show an example of the thread cleaning apparatus for carrying out the method for measuring a thread element at an end portion of a pipe relating to a third embodiment of the present invention.
Figure 8B:
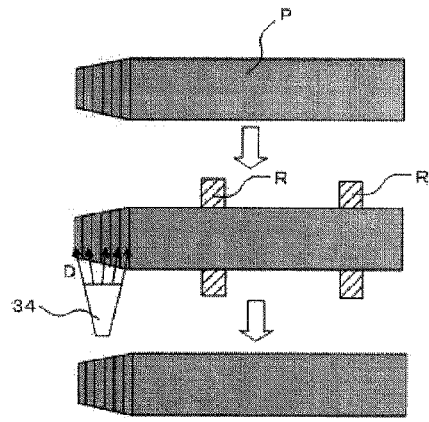
Figure 8C:
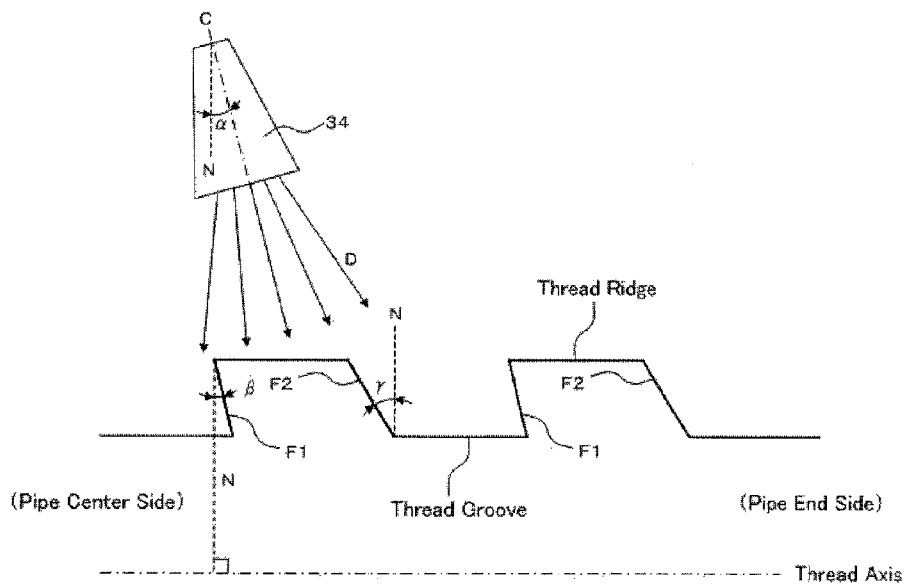

FIGS. 8A, 8B, and 8C are schematic diagrams to generally show an example of the thread cleaning apparatus for carrying out the method for measuring a thread element at an end portion of a pipe relating to a third embodiment of the present invention. FIG. 8A shows a front view, FIG. 8B shows a plan view, and FIG. 8C shows an enlarged sectional view in parallel with the pipe axial direction of the end portion of the pipe. As shown in FIGS. 8A, 8B, and 8C, a thread cleaning apparatus 30A of the present embodiment includes a nozzle 34 positioned above the pipe P. The nozzle 34 advances in the axial direction of the pipe P toward an end portion of the pipe P until the nozzle 34 is positioned above the threaded end portion of the pipe P. Then, after the advance action is finished, granular dry ice D and compressed air are supplied to the nozzle 34 from a supply source (not shown), and the granular dry ice D is ejected along with compressed air from the nozzle 34 toward the end portion of the pipe P. The dry ice D ejected from the nozzle 34 is sprayed in a linear shape along the axial direction of the pipe P. In this occasion, the pipe P is rotated in the circumferential direction by a turning roller R. Also, as needed, the nozzle 34 is moved in the axial direction of the pipe P. As a result of the above described actions, the entire circumference of the end portion of the pipe P is cleaned, and thereby it can be expected that any lubricant remaining on the end portion of the pipe during thread cutting and deburring, and cutting chips having adhered to the end portion of the pipe as a result of deburring are removed.

The present inventors have performed cleaning as an experiment by rotating the pipe P by one revolution under conditions that an ejection angle (an angle θ shown in FIG. 8A) of the dry ice D with respect to the vertical direction (a direction of V shown in FIG. 8A) was about 45°, a distance between the nozzle 34 and the pipe P was about 50 mm, a cleaning width (a width of the dry ice D sprayed in a linear shape) was about 40 mm, a cleaning length (a length of the dry ice D sprayed in a linear shape) was about 200 mm, an ejection pressure was about 0.35 MPa, and a rotational speed of the pipe P was about 10 rpm. The results have confirmed that any lubricant remaining on the end portion of the pipe during thread cutting and deburring, and cutting chips having adhered to the end portion of the pipe as a result of deburring are sufficiently removed.

Here, the rotational speed of the pipe P when an end portion of a pipe is cleaned is preferably set to about 5 rpm to 23 rpm. This is because, if the rotational speed is less than 5 rpm, dry ice D will be excessively sprayed onto the same site of the end portion of the pipe P and thereby dew condensation is likely to occur (thus impairing the advantage of the present embodiment that the drying step is obviated). On the other hand, if the rotational speed exceeds 23 rpm, there is risk that any lubricant remaining on the end portion of the pipe P during thread cutting and deburring, and cutting chips having adhered to the end portion of the pipe P as a result of deburring cannot be sufficiently cleaned.

Moreover, to prevent dew condensation caused by cleaning, it is preferable to set an upper limit to a number of revolutions of the pipe P during cleaning. This is because, if the number of revolutions is excessively large, the dry ice D is excessively sprayed on the same site on the end portion of the pipe P. This upper limit value, which varies depending on the rotational speed of the pipe P, is preferably not more than 1 revolution when the rotational speed is 5 rpm, and not more than 5 revolutions when the rotational speed is 23 rpm. The present inventors performed cleaning as an experiment under the above described conditions (ejection angle θ: about 45°, distance between the nozzle 34 and the pipe P: about 50 mm, the cleaning width: about 40 mm, the cleaning length: about 200 mm, the ejection pressure: about 0.35 MPa, and the rotational speed of the pipe P: about 10 rpm), and confirmed that dew condensation occurred when the pipe P was rotated by 3 revolutions (no dew condensation occurred at the number of revolutions of not more than 2).

Further, to effectively clean flank faces of a thread part formed at an end portion of the pipe P, it is preferable that the nozzle 34 is inclined according to the inclination angle of the flank face.

In a thread part when the pipe P is OCTG etc., as shown in FIG. 8C, both of the flank faces F1 and F2 which are located between a thread ridge and a thread groove are often inclined toward the pipe end side as the position moves from the thread ridge toward the thread groove. In other words, of the both flank faces F1 and F2, the flank face F2 on the pipe end side is inclined in such a way to move apart from the thread ridge as the position moves from the thread ridge to the thread groove, while the flank face F1 on the pipe center side is often inclined in such a way to move closer to the center of the thread ridge as the position moves from the thread ridge toward the thread groove. Then, if it is supposed that the inclination angle of the flank face F1 (an inclination angle with respect to a direction N perpendicular to the thread axis) is $\beta$ and the inclination angle of the flank face F2 (an inclination angle with respect to a direction N perpendicular to the thread axis) is $\gamma$, a condition: $\beta<\gamma$ is satisfied in many cases.

In this occasion, an inclination angle $\alpha$ of the nozzle 34 with respect to the thread axial direction (an angle formed by the ejection direction of the dry ice D from the nozzle 34 with respect to the direction N perpendicular to the thread axis (the center of the ejection direction is C)) is preferably set to satisfy a condition: $\beta<\alpha<\gamma$ so as to clean the flank faces F1, F2. For example, when $\beta=3°$ and $\gamma=10°$, the inclination angle $\alpha$ of the nozzle 34 is preferably set so as to be $3°<\alpha<10°$. Moreover, since the values of $\beta$ and $\gamma$ can take various values according to the uses of the pipe P, and the like, it is preferable that the value of the inclination angle $\alpha$ of the nozzle 34 is not fixed, but is variable. That is, the nozzle 34 is preferably placed so as to be freely inclined with respect to the thread axial direction of the pipe P (pipe axial direction).

As so far described, the present embodiment differs from the first and second embodiments in that the drying step is obviated since an end portion of a pipe is cleaned by ejecting granular dry ice D along with compressed air in the cleaning step. However, as for other configurations, since the present embodiment can appropriately adopt configurations similar to those of the first and second embodiments, the description thereof will be omitted herein.

REFERENCE SIGNS LIST

10 Thread cutting lathe
20 Deburring apparatus
30 Thread cleaning apparatus
40 Thread drying apparatus
50 Automatic thread element measurement apparatus
100 Thread processing line
P Pipe

The invention claimed is:

1. A method for automatically measuring a thread element at an end portion of a pipe or tube after thread processing is performed on the end portion of the pipe or tube, on a thread processing line in which thread processing is performed on the end portion of each pipe or tube which is successively conveyed, comprising:
   a cleaning step of cleaning the end portion of the pipe or tube after the thread processing is performed on the end portion of the pipe or tube;
   a drying step of drying the end portion of the pipe or tube after the end portion of the pipe or tube is cleaned in the cleaning step; and
   a measuring step of measuring the thread element at the end portion of the pipe or tube after the end portion of the pipe or tube is dried in the drying step, wherein
   the end portion of the pipe or tube is put under a clean atmosphere at least in the measuring step.

2. The method for measuring a thread element at an end portion of a pipe or tube according to claim 1, wherein
   the end portion of the pipe or tube is put under a clean atmosphere at least during a period from the drying step to the measuring step after thread processing is performed on the end portion of the pipe or tube.

3. The method for measuring a thread element at an end portion of a pipe or tube according to claim 1, wherein the clean atmosphere is under positive pressure when the end portion of the pipe or tube is put under the clean atmosphere.

4. A method for automatically measuring a thread element at an end portion of a pipe or tube after thread processing is performed on the end portion of the pipe or tube, on a thread processing line in which thread processing is performed on the end portion of each pipe or tube which is successively conveyed, comprising:
   a cleaning step of cleaning the end portion of the pipe or tube by ejecting granular dry ice with compressed air onto the end portion of the pipe or tube after thread processing is performed on the end portion of the pipe or tube; and
   a measuring step of measuring the thread element at the end portion of the pipe or tube after the end portion of the pipe or tube is cleaned in the cleaning step, wherein
   the end portion of the pipe or tube is put under a clean atmosphere at least in the measuring step.

5. The method for measuring a thread element at an end portion of a pipe or tube according to claim 4, wherein the clean atmosphere is under positive pressure when the end portion of the pipe or tube is put under the clean atmosphere.

* * * * *